(12) United States Patent
Sano et al.

(10) Patent No.: US 7,101,567 B1
(45) Date of Patent: Sep. 5, 2006

(54) CONTROLLED RELEASE PREPARATIONS HAVING MULTI-LAYER STRUCTURE

(75) Inventors: Akihiko Sano, Toyonaka (JP); Masako Kajihara, Itami (JP); Toshihiko Sugie, Toyonaka (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 09/701,303

(22) PCT Filed: May 19, 1999

(86) PCT No.: PCT/JP99/02594

§ 371 (c)(1),
(2), (4) Date: Nov. 28, 2000

(87) PCT Pub. No.: WO99/62501

PCT Pub. Date: Dec. 9, 1999

(30) Foreign Application Priority Data

May 29, 1998 (JP) .................................. 10-148591

(51) Int. Cl.
*A61F 2/00* (2006.01)
(52) U.S. Cl. ...................... 424/426; 424/425; 424/423; 424/422
(58) Field of Classification Search ................ 424/472, 424/426, 471, 468, 464
See application file for complete search history.

(56) References Cited

U.S. PATENT DOCUMENTS

| 4,351,337 | A |   | 9/1982  | Sidman |
|-----------|---|---|---------|--------|
| 4,601,893 | A | * | 7/1986  | Cardinal ..................... 424/424 |
| 4,985,253 | A |   | 1/1991  | Fujioka et al. |
| 5,011,692 | A | * | 4/1991  | Fujioka et al. ............. 424/426 |
| 5,558,879 | A | * | 9/1996  | Chen et al. .................. 424/480 |
| 5,776,481 | A |   | 7/1998  | Karst et al. |
| 5,851,547 | A | * | 12/1998 | Fujioka et al. ............. 424/426 |

FOREIGN PATENT DOCUMENTS

| EP | 0 009 410 A2 |   | 4/1980  |
|----|--------------|---|---------|
| EP | 0009410 A2   | * | 4/1980  |
| EP | 0 306 212 A2 |   | 3/1989  |
| EP | 0 659 406 A2 |   | 6/1995  |
| EP | 0659406      | * | 6/1995  |
| EP | 659406 A2    |   | 6/1995  |
| EP | 0722656 A1   |   | 7/1996  |
| JP | 62174031 A   |   | 7/1987  |
| JP | A62174031    |   | 7/1987  |
| JP | 04 364120 A  |   | 12/1992 |
| JP | A8331996     |   | 12/1996 |

OTHER PUBLICATIONS

Maeda et al., J. of Controlled Release, vol. 62, pp. 313-324, (1999).
Budavari et al., The Merck Index, 12th Edition, pp. 742-743, (1996).
Kajihara et al., J. of Controlled Release, vol. 66, pp. 49-61, (2000).

* cited by examiner

*Primary Examiner*—Gollamudi S. Kishore
*Assistant Examiner*—Pili A. Hawes
(74) *Attorney, Agent, or Firm*—Birch, Stewart, Kolasch & Birch, LLP (57) ABSTRACT

Preparations whereby two or more drugs can be released separately at appropriate speeds depending on the disease or the release behaviors of one or more drugs can be precisely controlled, which consist of an outer layer wherein a water-soluble drug is dispersed in a carrier made of a biologically non-degradable and hydrophobic polymer material, and one or more inner layers wherein a water-soluble drug, differing in kind or concentration from the one contained in the outer layer, is dispersed in a carrier made of a biologically non-degradable and hydrophobic polymer material, and in which the outer and inner layers are concentrically located in diametral direction of rod-like preparations and both or one of the ends in the axial direction are opened so as to directly come into contact with the environment.

8 Claims, 5 Drawing Sheets

CONTROLLED RELEASE PREPARATIONS HAVING MULTI-LAYER STRUCTURE

This application is the national phase under 35 U.S.C. § 371 of PCT International Application No. PCT/JP99/02594 which has an International filing date of May 19, 1999, which designated the United States of America.

THE FIELD OF THE INVENTION

The present invention relates to a controlled drug-release preparation useful for medicine and the livestock industry. More specifically, the present invention relates to a controlled drug-release preparation having multi-layer structure, whereby one or more drugs can separately be released with a different behavior in vivo, for the purpose of exhibiting effectively the efficacy thereof.

BACKGROUND OF THE INVENTION

A drug delivery system has been developed for the purpose of efficiently delivering an appropriate amount of a drug to a site with a disorder. For the purpose of adopting to individual purpose or disorder, a variety of the systems have been studied; for example, a controlled drug-release preparation using as a carrier a hydrophobic polymer material, which is non-degradable after administered into the living body. As a method of controlling release of a drug from such preparation, one using an additive such as an albumin (Japanese Patent publication (Tokkohei) No. 61959/1995), and one forming an outer layer consisting of hydrophobic polymer alone (Japanese Patent publication (Tokkaihei) No. 187994/1995) are disclosed. However, when a preparation contains several drugs, it is not possible to control the release of the drugs, by those techniques, so that each drug is released at a desired behavior from the preparation. The reasons thereof are as follows:

When a drug, of which release is to be controlled, is water-soluble, the powdery drug does not dissolve in a carrier but exists in a dispersed state therein. When such preparation is put in aqueous surroundings, the powdery drug present on the surface of the preparation dissolves in the surrounding water, and is released. Then, powdery drug present around a hole thus-formed dissolves to be released. Repetition of such phenomenon results in formation of a channel whereby the drug in the inside of the preparation is sequentially released. Thus, the drug-release behavior is influenced by physical features such as solubility or diffusion rate of drug into the aqueous surroundings. Accordingly, in a preparation wherein several drugs are homogeneously dispersed into a single carrier, it is impossible to respectively control the release of each drug as desired because the drug-release is influenced only by the physical features of the drugs.

Japanese Patent Publication (Tokkohei) No. 78017/1995 discloses a pulsatively controlled release preparation, which is designed so as to intermittently release one or more drugs. In this preparation, it is possible to control so that each drug is released at a different period of time, but not to separately control the release of several drugs during the same period of time. For some diseases, it will be more effective to release one or more drugs with a different behavior. However, as stated above it has never been achieved by a single preparation.

On the other hand, U.S. Pat. No. 4,351,337 discloses a biodegradable preparation with multi-layer structure wherein a poly-amino acid, which degrades by an enzyme in the living body, is used as a carrier, and wherein the drug is released by diffusion and degradation of a carrier. Accordingly, such biodegradable preparation with multi-layer structure has a problem, for example enzymes in the living body may influence its drug-release behavior.

Problem to be Solved by the Invention

The present invention has been done from the standpoint as stated above. An object of the present invention is to provide a preparation which can release two or more drugs separately at appropriate rates depending on disease or a preparation where the release behaviors of one or more drugs can be precisely controlled. Said problem to be solved has also been found by the inventors.

The Means to Solve the Problem

The inventors have eagerly studied for solving the problem and found that the followings are an essential key in releasing one or more drugs with different behavior: to form an implantable rod-like preparation in multi-layer structure, and to design it so that each layer is adapted to the most suitable arrangement and structure. In addition, by using as a carrier a biologically non-degradable hydrophobic polymer which does not degrade in vivo and is not influenced by enzyme etc., the preparation of the present invention can release stably the drug in vivo.

Thus, the present invention includes the following embodiments.

(1) A preparation which comprises an outer layer wherein a water-soluble drug is dispersed in a carrier comprising a biologically non-degradable hydrophobic polymer material, and one or more inner layer(s) wherein a water-soluble drug, which is different or different in concentration thereof from the drug contained in the outer layer, is dispersed in a carrier comprising a biologically non-degradable hydrophobic polymer material, and in which the outer and inner layer(s) are concentrically located in diametral direction of the rod-like preparation and both or one of the ends in the axial direction are open so as to directly come into contact with the environment.

(2) A preparation as stated in item (1) wherein a layer consisting of only biologically non-degradable hydrophobic polymer material exists between the inner layer in which a water-soluble drug is dispersed and the outer layer, or between two inner layers in which a water-soluble drug is dispersed.

(3) A preparation as stated in item (1) or (2) wherein each layer contains a different water-soluble drug.

(4) A preparation as stated in item (1) or (2) wherein each layer contains a different concentration of the same water-soluble drug.

(5) A preparation as stated in any one of items (1)–(4) wherein at least one of the outer layer or inner layer(s) contains two or more drugs.

(6) A preparation as stated in any one of items (1)–(5) wherein the biologically non-degradable hydrophobic polymer material is silicone.

MODE FOR CARRYING OUT THE INVENTION

In the present specification, an outer layer means the most outside layer in diametral direction of a rod-like preparation, i.e., one that directly contacts with the external environment in diametral direction.

Figure 1:
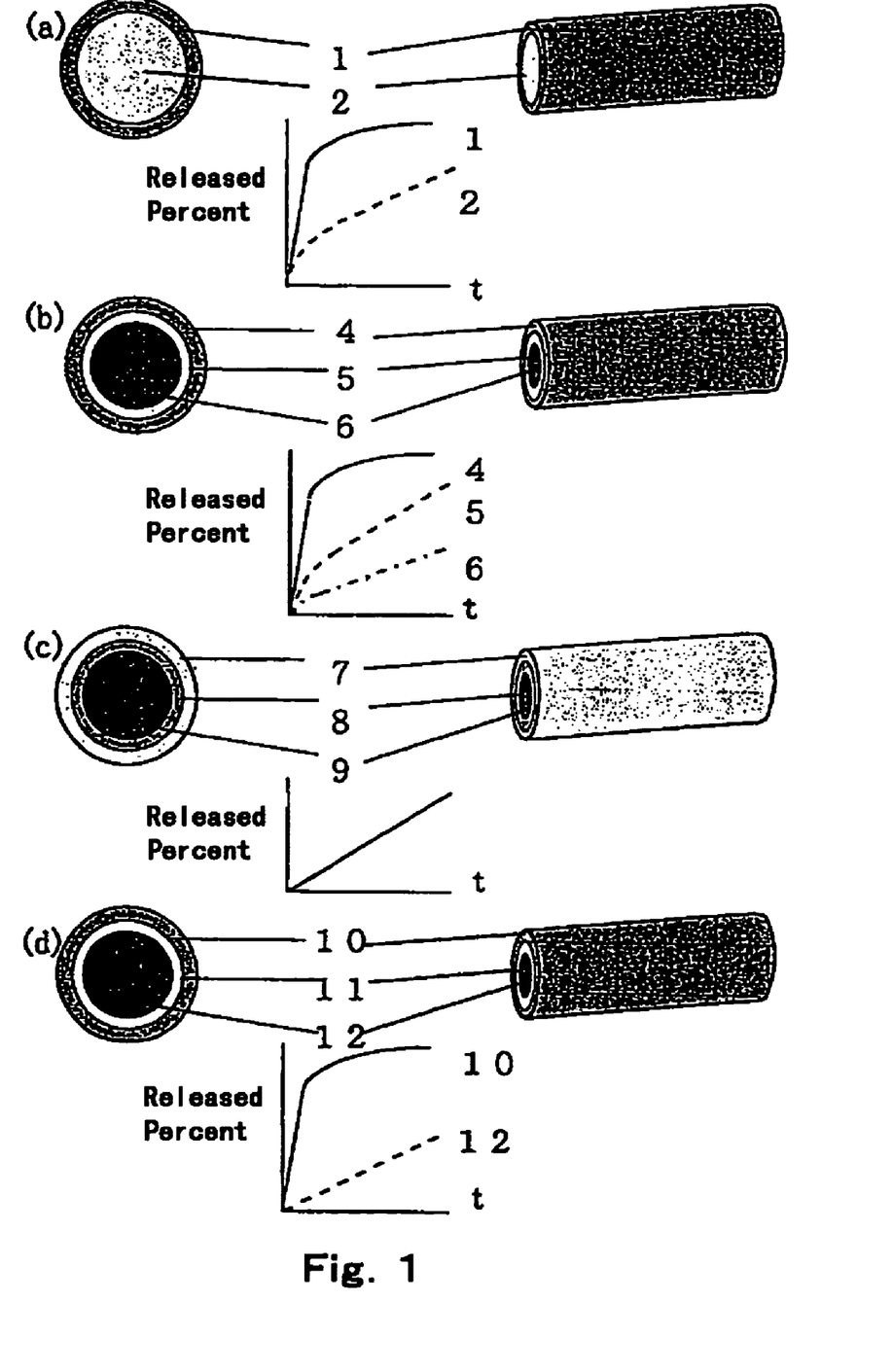
FIG. 1 represents cross sections and oblique views of the exemplified preparations of the present invention, and graphs showing time course of cumulative release percent of each drug from the preparations.

The exemplified preparations of the present invention are shown in FIG. 1 wherein a graph schematically representing time course of cumulative released amount of each drug from respective preparation are also shown.

In said figure, (a) represents a preparation wherein each layer contains a different kind of drugs respectively, 1 represents a layer containing one or more drugs, and 2 represents a layer containing one or more drugs other than those in 1.

(b) represents a preparation wherein each layer contains a different kind of drug respectively, 4 represents a layer containing one or more drugs, 5 represents a layer containing one or more drugs other than those in 4 and 6, and 6 represents a layer containing one or more drugs other than those in 4 and 5.

(c) represents a preparation wherein each layer contains a different concentration of the same kind of drug, 7 represents a layer containing one or more drugs, 8 represents a layer containing the same drug as that in 7 at a different concentration from those of the drugs in 7 and 9, and 9 represents a layer containing the same drug as that in 7 at a different concentration from those of the drugs in 7 and 8.

A graph showing time course of cumulative released amount shows a result in the case that the concentration of the drug in the layer is 7<8<9 in order.

(d) represents a preparation comprising a layer consisting of biologically non-degradable, hydrophobic polymer material alone between the drug-containing layers, 10 represents a layer containing one or more drugs, 11 represents a layer consisting of biologically non-degradable, hydrophobic polymer material alone, and 12 represents a layer containing the same drug as that in 10 at a different concentration from that in 10, or a layer containing a drug different from that in 10.

The different drug or the different kind of water-soluble drug used herein include the embodiment where drugs per se are different each other, or the embodiment where the combination of a plural of drugs are different. More specifically, in the case of the above (a), the following embodiments are included:

(1) Layer 1 contains drug A, and layer 2 contains drug B.

(2) Layer 1 contains drug A, and layer 2 contains drugs A and B.

(3) Layer 1 contains drugs A and B, and layer 2 contains drugs A and C.

(4) Layer 1 contains drugs A and B, and layer 2 contains drugs C and D.

The biologically non-degradable, hydrophobic polymer material are not limited so long as it is biocompatible. Silicones are preferred in view of easiness of molding, including, for example, Silastic™ Medical Grade ETR Elastomer Q7-4750 or Dow Corning™ MDX-4-4210 Medical Grade Elastomer. The other materials inclusive are ethylene-vinyl acetate copolymers, polyurethanes, polyethylenes, polytetrafluoroethylenes, polypropylenes, polyacrylates, polymethacrylates, and so on.

Any water soluble drug may be used in the present invention so long as it is water-soluble, and there is no restriction in term of molecular weight and so on. The drugs are exemplified by, but not limited to, cytokines such as interferons and interleukins; hematopoietic factors such as colony-stimulating factors and erythropoietin; hormones such as growth hormone, growth hormone releasing factor, calcitonin, luteinizing hormone, luteinizing hormone releasing hormone, and insulin; growth factors such as somatomedin, nerve growth factor, neurotrophic factors, fibroblast growth factor, and hepatocyte growth factor; cell adhesion factors; immunosuppressants; enzymes such as asparaginase, superoxide dismutase, tissue plasminogen activating factor, urokinase, and prourokinase; blood coagulating factors such as blood coagulating factor VIII; proteins involved in bone metabolism such as BMP (Bone Morphogenetic Protein); antigens which can be used for a vaccine for a human being and/or an animal; adjuvants; carcinoma antigens; nucleic acids; antibodies; anti-tumor agents such as adriamycin, bleomycin, mitomycin and so on; antibiotics; anti-inflammatory agents; alkylating agents, and the like. The interferon used herein may be $\alpha$-, $\beta$-, $\gamma$- or any other interferon, or any combination thereof. Interleukin may also be IL-1, IL-2, and IL-3 or any other one, and colony-stimulating factor may be multi-CSF (multipotential CSF), GM-CSF (granulocyte-macropharge CSF), G-CSF (granulocyte CSF), M-CSF (macrophage CSF), or any other one. Antigens are exemplified by, but not limited to, toxoid, vaccine, and live vaccine per se or a substance derived from them.

A layer in which any one of the drugs is homogeneously dispersed is concentrically located in diametral direction in order to obtain a desired release. For example, a drug, which is desired to be released at early stage, is to be located at an outer layer, and one, which is desired to bring out sustained release over an extended period of time, is to be located at more inner layer. Particularly, when sustained release over an extended period of time is desired, the layer in which the drug is dispersed may be located inside of a layer consisting of a carrier material alone. A layer consisting of a biologically non-degradable, hydrophobic polymer alone prevents from infiltration of water and release of a water-soluble drug, and therefore, in a layer existing inside thereof, the infiltration of water and release of the drug are restricted only at the axial end of the rod-like preparation, whereby the drug will be continuously released at a constant rate over a long period of time. For the preparation of the present invention, an additive can be used for the purpose of stabilizing or controlling release of a drug, if necessary. The additive is not critical as long as it is pharmaceutically acceptable, and include, but not limited to, salts such as sodium chloride and sodium citrate; amino acids such as glycine, alanine and sodium glutamate; sugars such as lactose and mannitol; and proteins such as gelatin, collagen, and albumin.

The ratio of a drug and an additive dispersed in a carrier to the total amount of the preparation is not critical as long as dispersion and molding is substantially possible, and preferably, the total amount of drug and additive is less than or equal to 50% by weight based on the weight of the preparation, preferably more than or equal to 5% and less than or equal to 40% by weight, and more preferably more than or equal to 25% and less than or equal to 35% by weight. The amount of the drug contained in the preparation, of course, may vary depending on a kind of a drug intended, a disorder to be treated, and so on.

The preparation of the invention should be rod-like shape, and comprises two or more layers in the cross section that is at right angles to axis of the preparation. The layers are concentrically located in diametral direction, and a kind of a drug and/or its content in each layer are different each other. An embodiment of the invention is shown in FIG. 1 which is a pictorial view of an external appearance and a cross section of the preparation of the invention.

The size of the preparation of the invention varies dependent on an animal to be administered or an administration region, and is preferably less than or equal to 10 mm in diameter and less than or equal to 50 mm in the axial length, and more preferably more than or equal to 0.5 mm and less than or equal to 5 mm in diameter and more than or equal to 3 mm and less than or equal to 35 mm in axial length. The thickness of each layer is determined dependent on the amount of a drug to be carried or a desired period of sustained release.

For preparing the preparation of the present invention, each layer may be prepared separately or simultaneously. For example, the most inner layer is molded in a rod-like shape, which is inserted into a rod-like mold with the same diameter as an outer diameter of the second layer with putting their centers together. Then, a carrier material containing a drug to be formed the second layer is poured into the mold and cured. After curing, the mold was removed to obtain the preparation of the present invention. The preparation of the present invention can also be obtained by molding the first layer, which is to be the most inner one of the preparation, in a rod-like shape, molding the second layer in a hollow tube-like shape, and then, combining the first layer and the second layer. These methods are used for preparing a preparation wherein the first layer is an inner layer and the second layer is an outer layer. Repetition of the same procedures can give a preparation having multiple inner layers. In addition, the preparation of the present invention can also be obtained by extruding an each layer of carrier material containing a drug, which is separately prepared, from a concentrically located nozzle. The method of the present invention is not limited to those methods.

While release behavior of a drug present in an outer layer is assumed to be similar to that of a preparation consisting of a single layer alone in view of the mechanism of dissolving a drug and forming a channel as stated above, the release behavior of a drug present in an inner layer has not yet been made clear. It has been found that in a preparation of the present invention comprising multiple layers arranged in diametrical direction of a rod-like preparation, wherein a water-soluble drug is dispersed in a carrier consisting of a biologically non-degradable hydrophobic polymer material, the drug in the outer layer is released at a fast rate from the early stage within a short period of time, and the drug present in the inner layer is released at the slower rate over the long period of time. When a layer consisting of only a biologically non-degradable hydrophobic polymer, to which water and a drug are not permeable, exists between an outer layer and an inner layer in which a water-soluble drug is dispersed, or between two inner layers in which a water-soluble drug is dispersed, the drug in the outer layer is quickly released in the first-order manner, and the drug in the inner layer can slowly be released in the zero-order manner over a long period of time. A rod-like preparation wherein two or more layers containing a different concentration of the same kind of drug are located in the diametrical direction can freely provide a complex release behavior.

The present preparation is useful for the treatment of, for example a cancer. Bleomycin prolongs S phase and blocks G2 phase in a cell cycle, and therefore, by administration of bleomycin all mitotic cells are synchronized to G2 phase. Under such a condition, administration of mitomycin, which is highly sensitive to G2 phase, allows killing of more mitotic cells. The preparation of the present invention, which contains bleomycin in the outer layer and mitomycin in the inner layer quickly releases bleomycin at an early stage whereby cells are synchronized, and then, leads to sustained release of mitomycin whereby cells in G2 phase are killed, and therefore, it is expected that a cancer can effectively treated by a single preparation. As other application example, there is treatment of fractures. Fibroblast growth factor (FGF) acts at a relatively early state of a recovery process to promote cartilage proliferation, but shows a suppressive effect in the subsequent cartilage calcification process, and therefore, it is undesirable that FGF exists at the fracture site for a long term. On the other hand, insulin-like growth factor-1 (IGF-1) has a maturation effect of bone cells. Accordingly, the preparation of the present invention, which contains FGF in the outer layer and IGF-1 in the inner layer, quickly releases FGF at the early stage to promote the growth of cartilage and matures a cartilage cell by IGF-1, whereby such a single preparation expectedly allows for providing an efficient treatment of a fracture.

As other application example, the present invention is useful for applying to a drug, which shows a therapeutic effect by down-regulation effect, such as LHRH agonist. Thus, LHRH agonist, when administered at a high dose, causes suppression of secretion of sex hormone by down-regulation of receptor, and thereafter, a condition of suppressed secretion of sex hormone are maintained by continuous administration of the agonist. A treatment of prostate carcinoma, endometriosis and so on has been performed by the method. The preparation of the present invention consisting of the most outer layer containing LHRH agonist, an intermediate layer consisting of a biologically non-degradable, hydrophobic polymer material alone, and an inner layer containing LHRH agonist quickly releases LHRH agonist in the most outer layer, while LHRH agonist in the inner layer can be continuously released, which leads to the optimum drug release behavior for this treatment.

The preparation of the present invention can also be used as a vaccine. A recent study has been reported that sustained release of an antigen substance by utilizing DDS technique leads to more effective activation of immune reaction rather than a usual aqueous injectable solution. In order to further enhance the effect, an adjuvant may be combined. An adjuvant is a generic term which shows a substance acts to enhance immunogenicity of an antigen while it does not have an antigenicity by itself. However, since an adjuvant may cause a strong inflammatory response to the injected region, it is undesirable to release the adjuvant for a long period as like as an antigen substance does. According to the present preparation, it can be controlled so that an adjuvant is quickly released at an early stage and an antigen is released for a long period, which leads to accumulation of immune cells in a specific region by the adjuvant and delivery of the antigen substance to said region over a long period of time. Thus, a safe and effective vaccine preparation may be obtained.

EXAMPLES

The present invention is illustrated by the following examples, but is not limited thereto.

Example 1

25 g of an aqueous ovalbumin (OVA) solution (100 mg/ml) was lyophilized. The lyophilized cake was milled under nitrogen atmosphere to obtain powder 1. To 386.8 g of an aqueous solution of interferon (IFN) (114 MU/ml), 16.8 g of bovine serum albumin (BSA) was mixed and the mixture was lyophilized. The lyophilized cake was milled under nitrogen atmosphere to obtain powder 2. Separately, 1.05 g of component A and 1.05 g of component B of Silastic™ Medical Grade ETR Elastomer Q7-4750 were mixed. After mixing, the mixture was quickly kneaded with 0.90 g of the above powder 1, which was filled to a syringe. Besides, 17.5 g of component A and 17.5 g of component B of Silastic™ Medical Grade ETR Elastomer Q7-4750 were mixed. After mixing, the mixture was quickly kneaded with 15.0 g of the above powder 2, which was filled to another syringe. The each filled product thus obtained was extruded with pressure through a nozzle with 1.6 mm in diameter and a nozzle with 1.9 mm in diameter, which were concentrically located, so that OVA-containing product and IFN-containing product become inner and outer respectively, which was allowed to stand at 25° C. for 3 days to cure. This was cut to provide the preparation 1 of the present invention.

Example 2

27.06 g of an aqueous solution of avidin (5 mg/ml), 1.73 g of an aqueous solution of sodium citrate (250 mg/ml), and 5.74 g of an aqueous solution of mannitol (150 mg/ml) were mixed and the mixture was lyophilized. The lyophilized cake was milled under nitrogen atmosphere to obtain powder 3. 57.45 g of an aqueous solution of IL-1 β (2 mg/ml) and 10.49 g of an aqueous solution of sodium citrate (250 mg/ml), and 35.01 g of an aqueous solution of mannitol (150 mg/ml) were mixed, and the mixture was lyophilized. The lyophilized cake was milled under nitrogen atmosphere to obtain powder 4. Separately, 1.05 g of component A and 1.05 g of component B of Silastic™ Medical Grade ETR Elastomer Q7-4750 were mixed. After mixing, the mixture was quickly kneaded with 0.90 g of the above powder 3, which was filled to a syringe. Besides, 8.4 g of component A and 8.4 g of component B of Silastic™ Medical Grade ETR Elastomer Q7-4750 were mixed. After mixing, the mixture was quickly kneaded with 7.20 g of the above powder 4, which was filled to another syringe. The each filled product thus obtained was extruded with pressure through a nozzle with 1.6 mm in diameter and a nozzle with 1.9 mm in diameter, which were concentrically located, so that avidin-containing product and IL-1 β-containing product become inner and outer respectively, which was allowed to stand at 25° C. for 3 days to cure. This was cut to provide the preparation 2 of the present invention.

Comparative Example 1

35.1 g of an aqueous solution of IFN (90 MU/ml), 47.2 g of an aqueous solution of human serum albumin (HSA) (78 mg/ml), 1.05 g of sodium glutamate, and 401.5 g of purified water were mixed, and the mixture was spray-dried. 1.8 g of component A and 1.8 g of component B of Silastic™ Medical Grade ETR Elastomer Q7-4750 were mixed. After mixing, the mixture was quickly kneaded with 2.4 g of the above powder, which was filled to a syringe. Besides, 50 g of component A and 50 g of component B of Silastic™ Medical Grade ETR Elastomer Q7-4750 were mixed, which was filled to another syringe. The each filled product thus obtained was extruded with pressure through a nozzle with 1.6 mm in diameter and a nozzle with 1.9 mm in diameter, which were concentrically located, so that drug-containing Silastic and Silastic alone become inner and outer respectively, which was allowed to stand at 37° C. for one week to cure. This was cut to provide the comparative preparation 1.

Comparative Example 2

To 1493.1 g of an aqueous solution containing at a concentration of 10.6 MU/ml of IFN and 10 mg/ml of HSA, 4.98 g of glycine was added, and the mixture was spray-dried. 0.9 g of component A and 0.9 g of component B of Silastic™ Medical Grade ETR Elastomer Q7-4750 were mixed. After mixing, the mixture was quickly kneaded with 1.2 g of the above powder. The obtained mixture was filled to a syringe, and extruded with pressure through a hole with 1.6 mm in diameter, which was allowed to stand at 37° C. for one week to cure. This was cut to provide the Comparative Preparation 2.

Experiment 1

Figure 2:
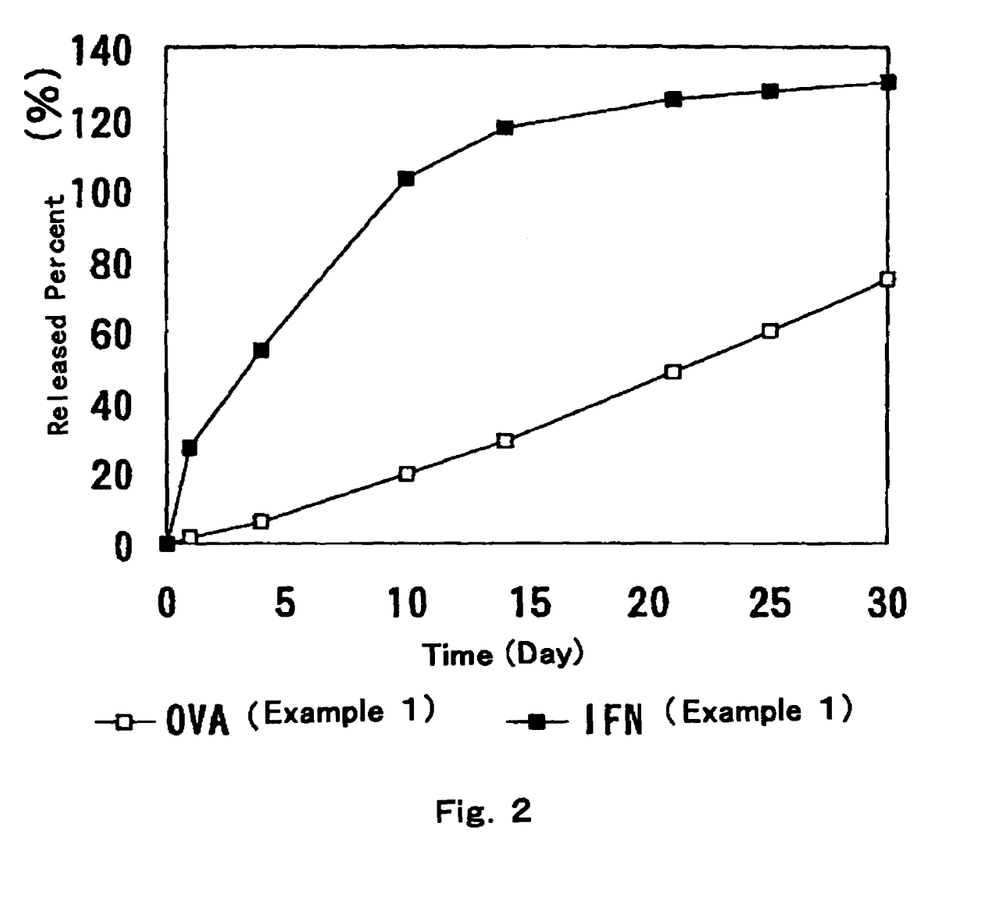
FIG. 2 represents a graph showing time course of the cumulative release percent of OVA and IFN from the preparation of Example 1 in Experiment 1.

A preparation of Example 1, which was cut to 1 cm in length, was put into 2 ml of phosphate buffer (pH 7.4) containing 0.3% Tween 20 and 0.01% sodium azide and allowed to stand, from which released OVA and IFN were determined by ELISA and RIA respectively, and then, accumulated released rate was obtained. The results are shown in FIG. 2.

Experiment 2

Figure 3:
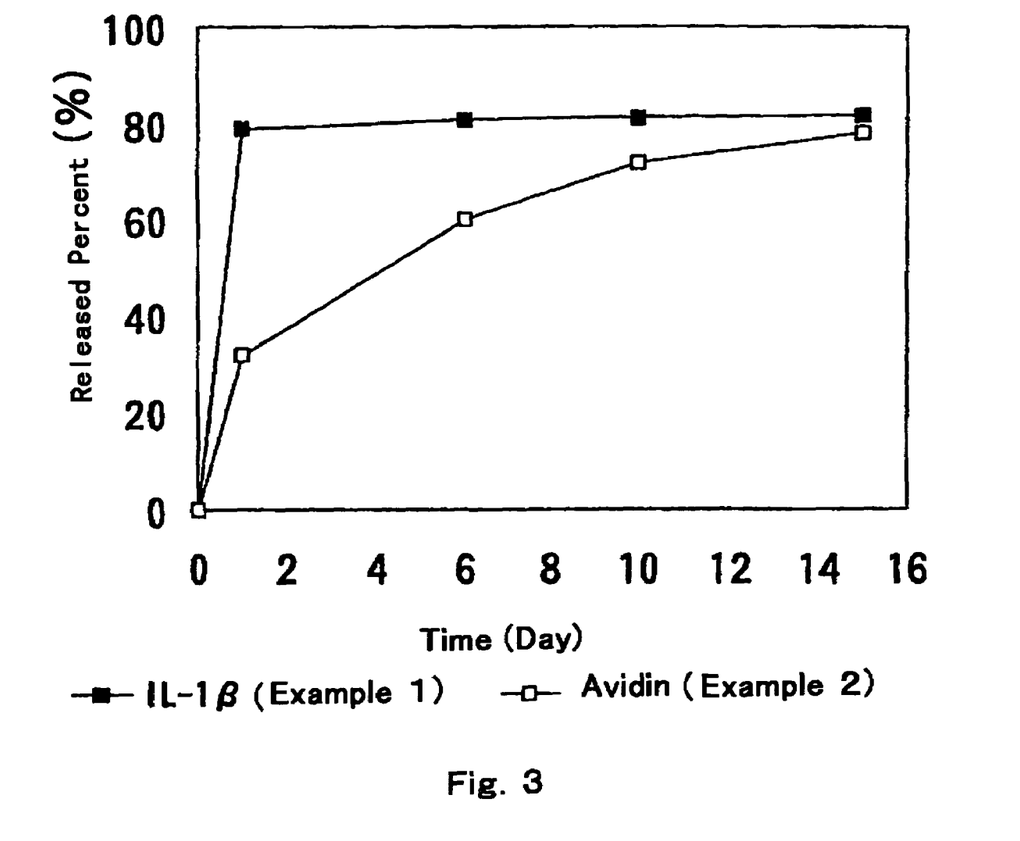
FIG. 3 represents a graph showing time course of the cumulative release percent of IL-1 and avidin from the preparation of Example 2 in Experiment 2.

A preparation of Example 2, which was cut to 1 cm in length, was put into 2 ml of phosphate buffer (pH 7.4) containing 0.3% Tween20 and 0.01% sodium azide and allowed to stand, from which released avidin and IL-1 β were respectively determined by ELISA, and then, accumulated released rate was obtained. The results are shown in FIG. 3.

Experiment 3

Figure 4:
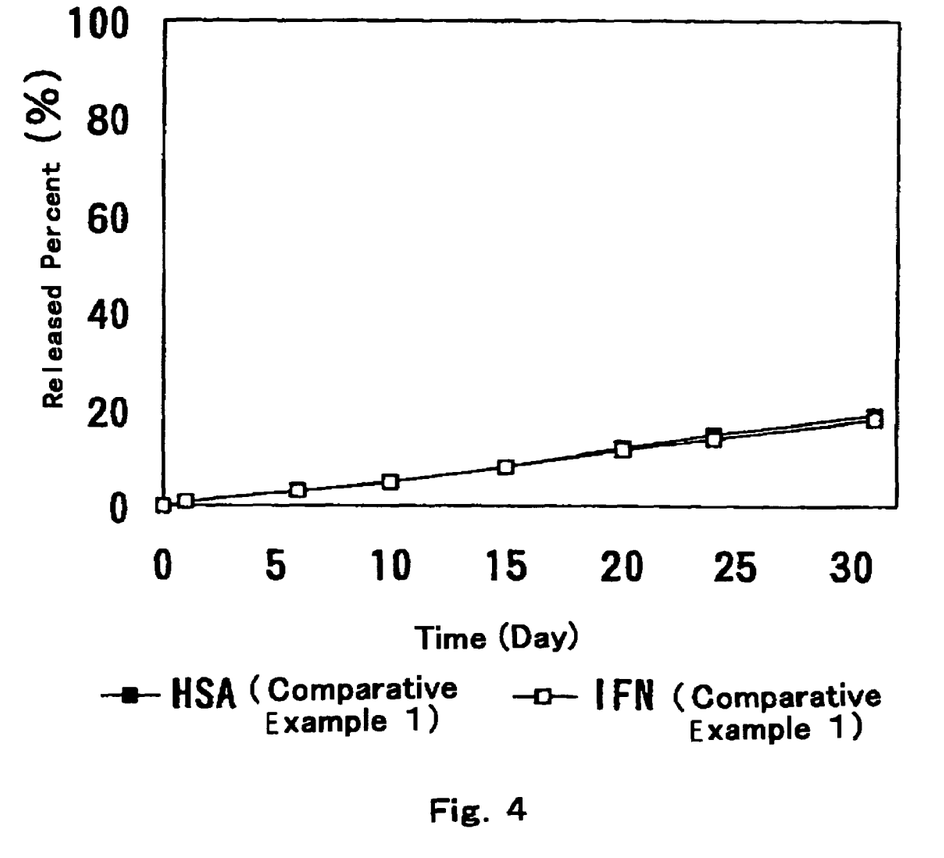
FIG. 4 represents a graph showing time course of the cumulative release percent of HSA and IFN from the preparation of Comparative Example 1 in Experiment 3.

A preparation of Comparative Example 1, which was cut to 1 cm in length, was put into 10 ml of phosphate buffer (pH 7.4) containing 0.5% BSA and 0.01% sodium azide and allowed to stand, from which released HSA and IFN were determined by ELISA and RIA respectively, and then, accumulated released rate was obtained. The results are shown in FIG. 4.

Experiment 4

Figure 5:
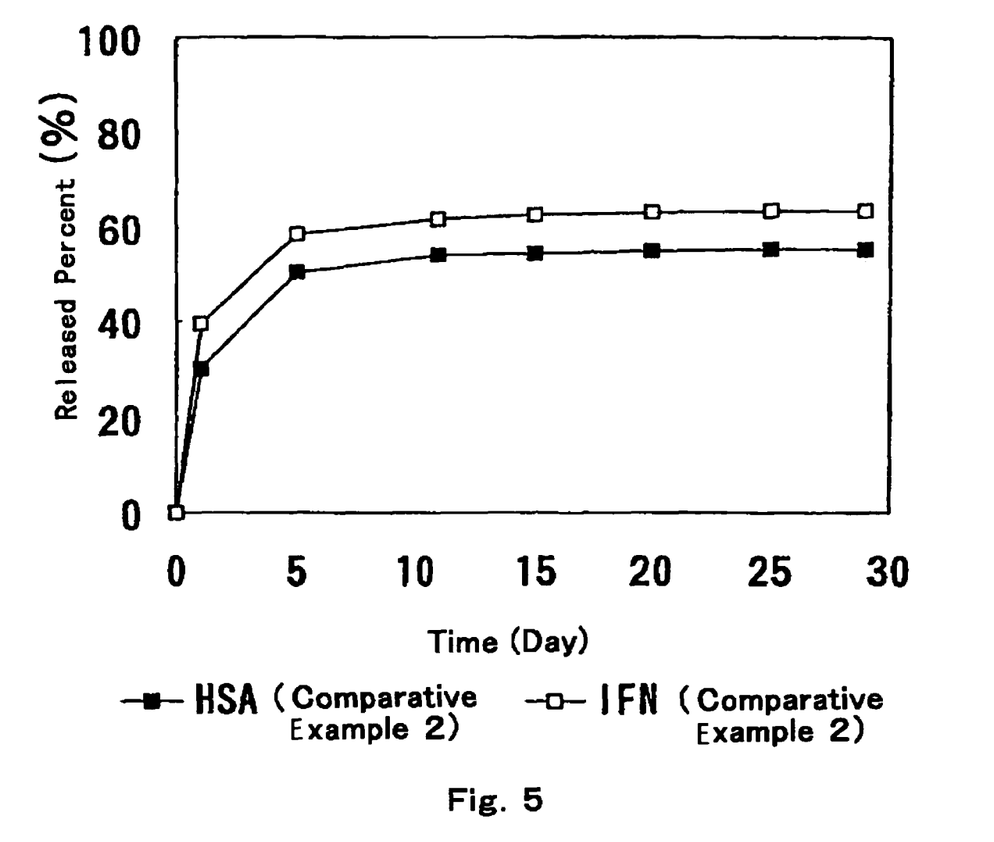
FIG. 5 represents a graph showing time course of cumulative release percent of HSA and IFN from the preparations of Comparative Example 2 in Experiment 4.

A preparation of Comparative Example 2, which was cut to 1 cm in length, was put into 10 ml of phosphate buffer (pH 7.4) containing 0.5% BSA and 0.01% sodium azide and allowed to stand, from which released HSA and IFN were determined by ELISA and RIA respectively, and then, accumulated released rate was obtained. The results are shown in FIG. 5.

The preparation of the present invention enabled a separate control of release behaviors for IFN and OVA. Thus, release of a drug present in the outer layer (IFN in Example 1 and IL-1 β in Example 2) was completed at an early stage, while a drug present in the inner layer (OVA in Example 1 and avidin in Example 2) showed a sustained release during the period for determination (FIGS. 2 and 3). On the other hand, the preparations of Comparative Examples 1 and 2 released IFN and HSA in the same pattern.

Example 3

A mixture of OVA and Silastic™, Silastic™ alone, and a mixture of IFN, BSA and Silastic™, obtained in Example 1, are extruded with pressure from a nozzle with 5 mm in outer diameter, which has a concentric structure, so that each of those ingredients formed the most inner, intermediate, and the most outer layers respectively, which is then allowed to stand at 25° C. for 3 days to cure. This is cut to provide the preparation 3 of the present invention.

Example 4

3.62 g of an aqueous IFN solution (50 MU/ml), 1 g of HSA powder and 15.38 ml of purified water are mixed, and the mixture is lyophilized. The lyophilized cake is milled under nitrogen atmosphere to obtain powder 5. 1.05 g of component A and 1.05 g of component B of Silastic™ Medical Grade ETR Elastomer Q7-4750 are mixed. After mixing, the mixture is quickly kneaded with 0.90 g of the powder 5. 56.0 ml of an aqueous solution of interferon (IFN) (50 MU/ml) and 1 g of HSA powder are mixed, and the mixture is lyophilized. The lyophilized cake is milled under nitrogen atmosphere to obtain powder 6. 1.05 g of component A and 1.05 g of component B of Silastic™ Medical Grade ETR Elastomer Q7-4750 are mixed. After mixing, the mixture is quickly kneaded with 0.90 g of the powder 6. 347 ml of an aqueous solution of interferon (IFN) (100 MU/ml) and 0.6 g of HSA powder are mixed, and the mixture is lyophilized. The lyophilized cake is milled to obtain powder 7. 0.35 g of component A and 0.35 g of component B of Silastic™ Medical Grade ETR Elastomer Q7-4750 are mixed. After mixing, the mixture is quickly kneaded with 0.30 g of the above powder 7. A mixture of powder 7 and Silastic™, a mixture of powder 6 and Silastic™, and a mixture of powder 5 and Silastic™ are extruded with pressure through a nozzle with 2 mm in outer diameter, which has a concentric structure, so that those ingredients form the most inner, intermediate, and the most outer layers respectively, which is then allowed to stand at 25° C. for 3 days to cure. This is cut to provide the preparation 4 of the present invention.

Example 5

5 ml of influenza A antigen (Chemicon, catalog. No. AG-845), 1.87 g of an aqueous solution of sodium citrate (250 mg/ml), 6.22 g of aqueous mannitol solution (150 mg/ml) and 20 g of purified water are mixed, and the mixture is lyophilized. The lyophilized cake is milled under nitrogen atmosphere to obtain powder 8. 29.63 g of an aqueous solution of IL-2 (1 mg/ml), 10.63 g of an aqueous solution of sodium citrate (250 mg/ml), 35.42 g of an aqueous mannitol solution (150 mg/ml) and 110.45 g of purified water are mixed, and the mixture is lyophilized. The lyophilized cake is milled under nitrogen atmosphere to obtain powder 9. 1.05 g of component A and 1.05 g of component B of Silastic™ Medical Grade ETR Elastomer Q7-4750 are mixed. After mixing, the mixture is quickly kneaded with 0.90 g of the powder 8, which is filled into a syringe. 8.4 g of component A and 8.4 g of component B of Silastic™ Medical Grade ETR Elastomer Q7-4750 are mixed. After mixing, the mixture is quickly kneaded with 7.20 g of the powder 9, which is filled into another syringe. The filled products thus obtained is extruded with pressure through a nozzle with 1.6 mm in diameter and a nozzle with 1.9 mm in diameter, which are concentrically located, so that influenza-containing product and IL-2-containing product form inner and outer layers respectively, which is then allowed to stand at 25° C. for 3 days to cure. This is cut to provide the preparation 5 of the present invention.

Example 6

Bleomycin hydrochloride powder is milled under nitrogen atmosphere to obtain powder 10. Mitomycin C powder is milled under nitrogen atmosphere to obtain powder 11. 8.4 g of component A and 8.4 g of component B of Silastic™ Medical Grade ETR Elastomer Q7-4750 are mixed. After mixing, the mixture is quickly kneaded with 7.2 g of the above powder 10, which is filled into a syringe. Then, 8.4 g of component A and 8.4 g of component B of Silastic™ Medical Grade ETR Elastomer Q7-4750 are mixed. After mixing, the mixture is quickly kneaded with 7.2 g of the powder 11, which is filled into another syringe. The filled products thus obtained is extruded with pressure through a nozzle with 1.9 mm in diameter and a nozzle with 2.3 mm in diameter, which are concentrically located, so that mitomycin C-containing product and bleomycin hydrochloride-containing product form inner and outer layers respectively, which is allowed to stand at 25° C. for 3 days to cure. This is cut to provide the preparation 6 of the present invention.

Example 7

20.17 ml of insulin-like growth factor (IGF-1), 1.84 g of an aqueous solution of sodium citrate (250 mg/ml), 6.13 g of an aqueous mannitol solution (150 mg/ml) and 25 g of purified water are mixed, and the mixture is lyophilized. The lyophilized cake is milled under nitrogen atmosphere to obtain powder 12. 35.90 mg of basic fibroblast growth factor (bFGF), 1.82 g of an aqueous solution of sodium citrate (250 mg/ml), 6.06 g of an aqueous mannitol solution (150 mg/ml) and 24.67 g of purified water are mixed, and the mixture is lyophilized. The lyophilized cake is milled under nitrogen atmosphere to obtain powder 13. 1.05 g of component A and 1.05 g of component B of Silastic™ Medical Grade ETR Elastomer Q7-4750 are mixed. After mixing, the mixture is quickly kneaded with 0.90 g of the powder 12, which is filled into a syringe. 1.05 g of component A and 1.05 g of component B of Silastic™ Medical Grade ETR Elastomer Q7-4750 are mixed. After mixing, the mixture is quickly kneaded with 0.90 g of the powder 13, which is filled into another syringe. The filled products thus obtained are extruded with pressure through a nozzle with 1.6 mm in diameter and a nozzle with 1.9 mm in diameter, which are concentrically arranged, so that IGF-1-containing product and bFGF-containing product form inner and outer layers respectively, which is then allowed to stand at 25° C. for 3 days to cure. This is cut to provide the preparation 7 of the present invention.

What is claimed is:

1. A preparation which comprises an outermost layer wherein a water-soluble drug is dispersed in a carrier comprising a biologically non-degradable hydrophobic polymer material, and one or more inner layer(s) wherein a water-soluble drug, which is different or different in concentration thereof from the drug contained in the outermost layer, is dispersed in a carrier comprising a biologically non-degradable hydrophobic polymer material, and in which the outermost and inner layer(s) are concentrically located in diametral direction of a rod-like preparation, both or one of the ends in axial direction are open so as to directly come into contact with the environment and the outermost layer directly contacts with the environment in the diametrical direction.

2. A preparation which comprises an outermost layer wherein a water-soluble drug is dispersed in a carrier comprising a biologically non-degradable hydrophobic polymer material, and one or more inner layer(s) wherein a water-soluble drug, which is different or different in concentration thereof from the drug contained in the outermost layer, is dispersed in a carrier comprising a biologically non-degradable hydrophobic polymer material, and in which the outermost and inner layer(s) are concentrically located in diametral direction of a rod-like preparation, both or one of the ends in axial direction are open so as to directly come into contact with the environment and the outermost layer directly contacts with the environment in the diametrical direction, and wherein a layer consisting of only biologically non-degradable hydrophobic polymer material exists between the one or more inner layer(s) in which a water-soluble drug is dispersed and the outermost layer, or between two inner layers in which a water-soluble drug is dispersed.

3. A preparation as claimed in claim 1 or 2, wherein each of the outermost layer and the inner layer(s) in which a water-soluble drug is dispersed, contains a different water-soluble drug.

4. A preparation as claimed in claim 1 or 2, wherein each of the outermost layer and the inner layer(s) in which a water-soluble drug is dispersed, contains a different concentration of the same water-soluble drug.

5. A preparation as claimed in claim 1, wherein at least one of the outermost layer or inner layer(s) contains two or more water-soluble drugs.

6. A preparation as claimed in claim 1, wherein the biologically non-degradable hydrophobic polymer is silicone.

7. A preparation as claimed in claim 2, wherein at least one of the outermost layer or inner layer(s) contains two or more water-soluble drugs.

8. A preparation as claimed in claim 2, wherein the biologically non-degradable hydrophobic polymer material is silicone.

* * * * *